United States Patent [19]

Sanford

[11] Patent Number: Plant 6,937

[45] Date of Patent: Jul. 18, 1989

[54] SPIDER CHRYSANTHEMUM NAMED AUTUMN CHAMPAGNE

[76] Inventor: Randall L. Sanford, 2335 Bautista Ave., Vista, Calif. 92084

[21] Appl. No.: 220,732

[22] Filed: Jul. 18, 1988

[51] Int. Cl.[4] ..... A01H 5/00

[52] U.S. Cl. ..... Plt./79

[58] Field of Search ..... Plt./79–80

*Primary Examiner*—Robert E. Bagwill

*Attorney, Agent, or Firm*—Charles W. Rummler

[57] ABSTRACT

A new variety of Chrysanthemum morifolium of the incurved, spider type distinguished by its very large blooms having abundant ray florets of a light salmon color and carried on very tall stems, which are disbudded to present a single bloom with abundant foliage, the plant having a nine-week response with a moderate growth rate.

2 Drawing Sheets

BACKGROUND OF THE NEW PLANT

This new variety of Chrysanthemum was discovered by me as a sport of the variety 'CF 4730 Pink Spider' (unpatented) growing in my nursery at Vista, Calif., and was selected for propagation because of its rather unusual flower color of a light salmon rather than pink, and asexual propagation was carried on through several successive generations by means of cuttings at Vista, and also at Carpinteria, Calif., whereby this new cultivar has been found to retain its distinctive characteristics from generation to generation, which appear to be firmly fixed.

DESCRIPTION OF THE DRAWINGS

My new variety of chrysanthemum plant is illustrated by the accompanying drawings, which show the form and color characteristics of the flower and foliage as nearly true as is reasonably possible to obtain by means of conventional photographic procedures, sheet one of the drawings showing a plurality of individual stems with flowers in successive stages of development from a newly opening bud to a fully developed bloom; and sheet two of the drawings shows a side-by-side comparison of the new flower with the bloom of the parent variety, the new variety being at the right of the parent.

DESCRIPTION OF THE NEW PLANT

The following is a detailed description of my new variety of chrysanthemum plant with the color designations according to The R.H.S. Colour Chart published by The Royal Horticultural Society of London, England.

THE PLANT

Origin: Sport.
Parentage: 'CF 4730 Pink Spider' (unpatented).
Classification:
- *Botanic.*—*Chrysanthemum morifolium.*
- *Commercial.*—Incurved spider.

Form: Perennial herbaceous bush.
Height: About 150 cm.
Growth: Terminal. Vigorous, sturdy and upright, with good strength.
Branching: Average.
Foliage:
- *Quantity.*—Abundant.

- *Number of leaves.*—About 30 to 38, depending upon day length.
- *Leaf size.*—Large.
- *Leaf shape.*—Lobed with margins having widely spaced serrations.
- *Venation.*—Prominently veined pinnately.
- *Color.*—Upper side — Yellow-Green, 147-A. Under side — 147-B.
- *Petiolules.*—Length: About 3 to 4 cm.

THE BUD

Form: Globular.
Size: Large.
- *Diameter.*—About 2 cm.
- *Length.*—About 1.5 cm.

Opening rate: Average.
Color: When phyllaries first divide and when petals begin to unfurl, Green, 137-C.
Phyllaries:
- *Shape.*—Spear-shaped.
- *Number.*—About 55.
- *Character.*—Hooded over the bud, attached at the base and separated at the distal ends. When flowers open, the phyllaries stand up.
- *Color.*—Dark green. Inside — Green, 137-C. Outside — 137-B.

Calyx:
- *Shape.*—Round.
- *Size.*—Large.
- *Splitting.*—The calyx splits.
- *Aspect.*—Slightly pubescent.

Flower stem:
- *Length.*—About 150 cm.
- *Character.*—Rigid and slightly pubescent. Color: Yellow Green, 146-D.

Blooming habit:
- *Natural.*—mid-Fall. Recurrent with controlled photoperiod.

Response: About nine weeks.
Blooms: Borne singly on a disbudded stem.
- *Form.*—When bloom first opens, cup-shaped. When bloom matures, nearly round.

Petalage:
- *Number of phyllaries.*—About 55.
- *Number of florets.*—Ray florets — About 310. Disc florets — About 32. Arrangement: Whorled on a receptacle. Form: Recurved tubed-petal spider. Margin type: Smooth. Texture: Soft. Aspect:

Velvety. Color: As observed in Spring: Outer florets:

| | Three Quarter Open | Fully Open |
|---|---|---|
| Body: | Greyed Red, 179-B | Salmon, 27-B |
| Base: | Green-Yellow, 1-C | Sap Green, 150-B |
| Inside Petal Tube: | Red-Purple, 60-C | Striated Red-Purple, 59-D over Red, 54-D |
| Petal Tip: | Yellow-Orange, 19-B | Yellow, 9-C |

Discoloration after full bloom: Loss of magenta factor as the bloom ages.

Effect of weather: The color fades in hot weather.

Persistence: The flower hangs on and dries.

Disease resistance: More resistant to Botrytis than the parent 'CF 4730 Pink Spider'.

Lasting quality: As a cut flower, good. The petals stay on the stem three to four weeks.

THE REPRODUCTIVE ORGANS

Stamens:

*Number.*—Five.

*Arrangement.*—Whorled.

*Anthers.*—Indistinct. Color: Greyed Orange, 163-A.

*Filaments.*—Length: About 2 mm. Color: White.

*Pollen.*—None.

Pistils: One per floret.

*Styles.*—Length: About 12 mm. Color: Yellow-Green, 151-C.

*Stigmas.*—Color: Yellow, 13-A.

Character of ovaries: Small, round, and white.

My new cultivar is similar in many respects to the unpatented cultivar 'CF 4730 Pink Spider' with respect to flower form and size; foliage size and shape and color; and plant height or growth.

My new cultivar is distinguished from 'CF 4730 Pink Spider', however, when grown under comparable conditions, by the fact that the flower color is of a bronzed appearance rather than a pink and the flower is more resistant to Botrytis.

I claim:

1. The new and distinct spider type Chrysanthemum substantially as herein shown and described, particularly distinguished by the abundance of the incurved ray florets, the very large size of its blooms, and its resistance to Botrytis.

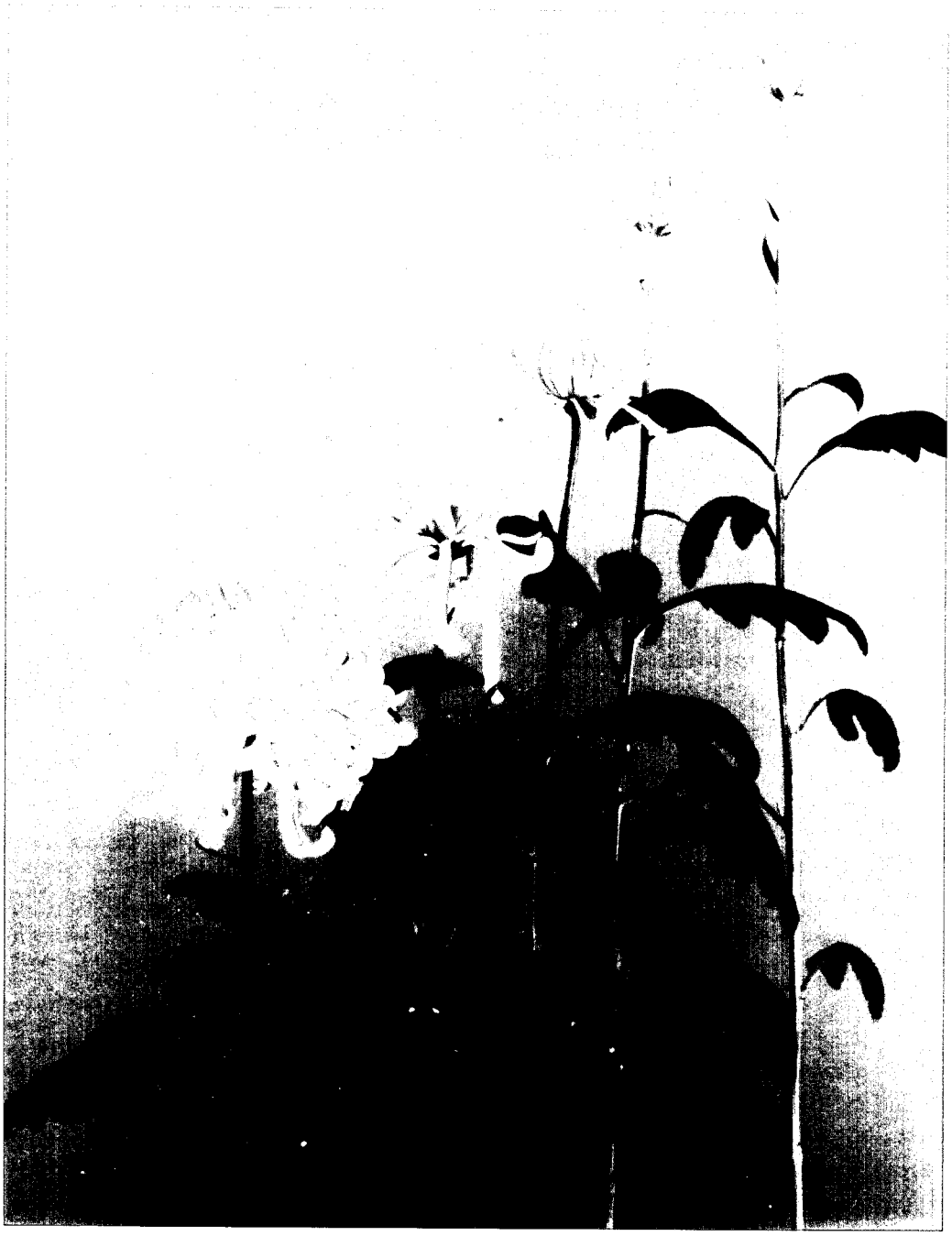

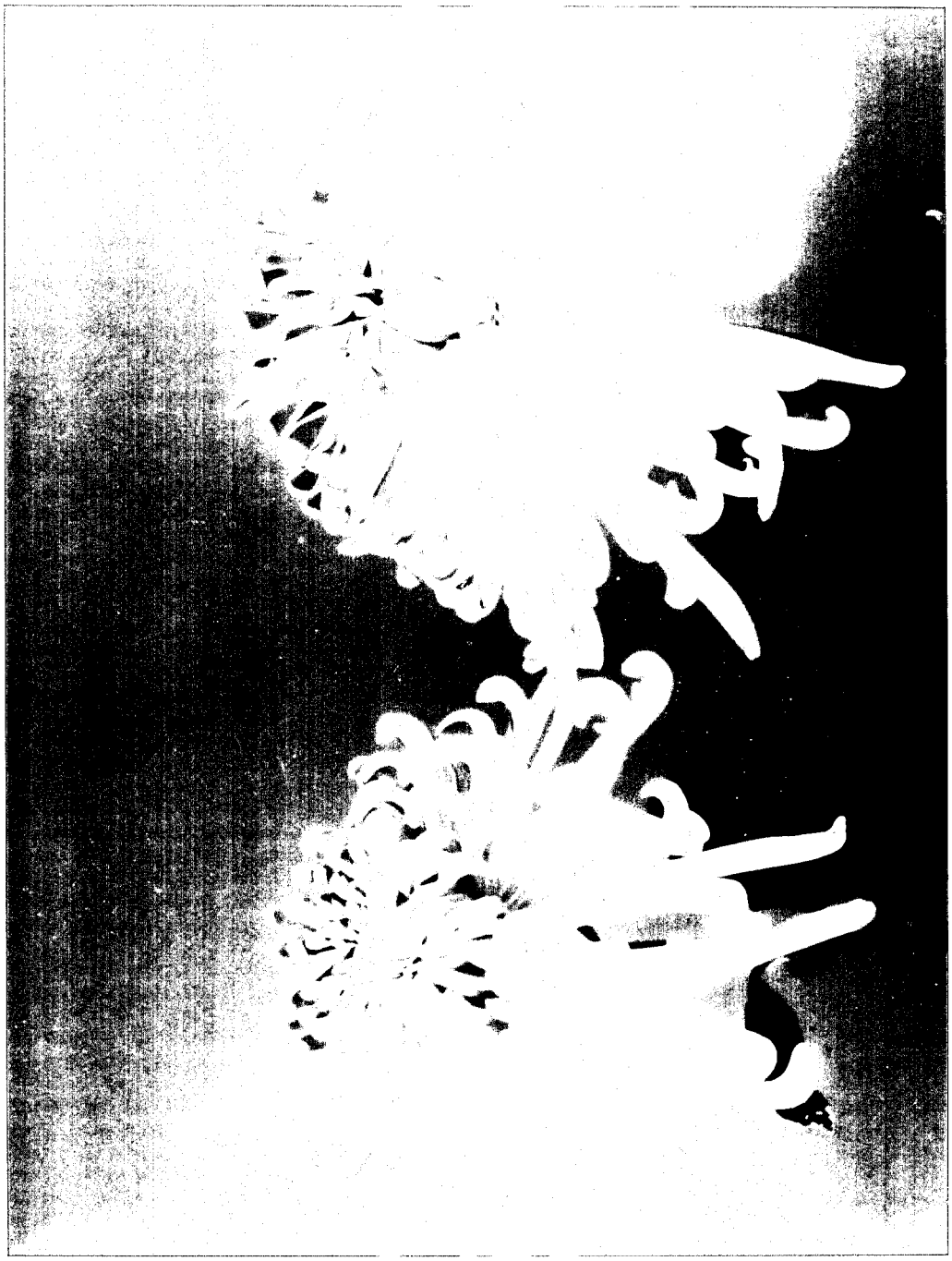

* * * * *